US006585075B1

(12) United States Patent
Gauthier

(10) Patent No.: US 6,585,075 B1
(45) Date of Patent: Jul. 1, 2003

(54) HEARING AID HAVING HARD MOUNTED SPEAKER AND ENERGY ABSORBING TIP

(76) Inventor: Edouard A. Gauthier, 109 Mt. Hunger Shore Rd., Windham, ME (US) 04062

( * ) Notice: Subject to any disclaimer, the term of this patent is extended or adjusted under 35 U.S.C. 154(b) by 0 days.

(21) Appl. No.: 09/694,201

(22) Filed: Oct. 23, 2000

(51) Int. Cl.[7] .......................... A61B 7/02; H04R 25/00; H04R 25/02

(52) U.S. Cl. ...................... 181/135; 181/129; 181/130; 381/312; 381/322; 381/324; 381/325; 381/328

(58) Field of Search ................................ 181/129, 130, 181/135; 381/312, 322, 323, 324, 325, 326, 327, 328

(56) References Cited

U.S. PATENT DOCUMENTS 3,374,318 A * 3/1968 Martin ....................... 381/325
3,448,224 A * 6/1969 Giller ......................... 381/328
3,852,540 A * 12/1974 Diethelm .................... 381/324
4,375,016 A * 2/1983 Harada ....................... 181/135
4,532,649 A * 7/1985 Bellafiore ................... 381/324
4,553,627 A * 11/1985 Gastmeier et al. .......... 181/135
4,584,437 A * 4/1986 Giannetti .................... 381/328
4,706,778 A * 11/1987 Topholm .................... 181/135
4,739,512 A * 4/1988 Hartl et al. ................. 381/328
4,870,689 A * 9/1989 Weiss ......................... 381/325
4,937,876 A * 6/1990 Biermans .................... 381/324
4,962,537 A * 10/1990 Basel ........................ 381/328
4,969,534 A * 11/1990 Kolpe et al. ................ 181/130
5,166,659 A * 11/1992 Navarro ...................... 381/325
5,742,692 A * 4/1998 Garcia et al. ............... 381/328
5,748,743 A * 5/1998 Weeks ........................ 381/328
6,144,749 A * 11/2000 Fideler ....................... 381/323
6,212,283 B1 * 4/2001 Fletcher et al. ............. 381/313
6,310,961 B1 * 10/2001 Oliveira et al. ............. 381/328

* cited by examiner

*Primary Examiner*—Robert E. Nappi
*Assistant Examiner*—Patrick Miller
(74) *Attorney, Agent, or Firm*—RatnerPrestia

(57) ABSTRACT

A hearing aid having a speaker that is hard mounted to the housing of the hearing aid and has an energy absorbing tip at that end of the hearing aid that is innermost in the ear and closest to the ear canal of the person wearing the hearing aid. According to another aspect of the present invention, the open end of the sound outlet through which an amplified version of the input sound is conducted is remote from that end of the hearing aid that is innermost in the ear and closest to the ear canal of the person wearing the hearing aid.

22 Claims, 4 Drawing Sheets

HEARING AID HAVING HARD MOUNTED SPEAKER AND ENERGY ABSORBING TIP

TECHNICAL FIELD

The present invention relates, in general, to hearing aids and, in particular, to a hearing aid having a speaker that is mounted rigidly to the hearing aid housing and an energy absorbing tip that absorbs mechanical and acoustic energy from the speaker that might otherwise create undesired feedback.

BACKGROUND OF THE INVENTION

FIG. 1 is a schematic sectional view of a conventional hearing aid. This hearing aid includes a housing 10 having a sound inlet 12 extending through a faceplate 13 of the housing and through which outside sound reaches a microphone 14. The microphone develops an electrical signal representative of the outside sound and the microphone signal is conducted to an amplifier 16 that amplifies the microphone signal. Amplifier 16 is powered by a battery 18 that is held in a battery holder 20 mounted for pivotal movement about a hinge 22 on housing 10. Battery holder 20 is held in place by a battery snap 24 on housing 10.

The amplified microphone signal is conducted to a speaker 26, commonly referred to as a receiver when used in a hearing aid, that develops an audio output of the amplified microphone signal. The audio output is conducted through a speaker sound outlet 28 and a housing outlet 30, defined by a tube 32, into the ear canal of the person wearing the hearing aid.

Speaker 26 is held in a resilient suspension 34 that is mounted to housing 10 by tube 32. Tube 32 is generally flexible but is sufficiently stiff to support resilient suspension 34. As shown in FIG. 1, resilient suspension 34 is spaced from housing 10 by spaces 36 and 38 that surround the resilient suspension. Resilient suspension 34, tube 32 and spaces 36 and 38 serve to isolate vibrations generated by speaker 26 when the speaker is driven to create the audio output.

One of the constraints of existing hearing aid designs, such as the one shown in FIG. 1, is that of internal feedback. A hearing aid is designed with: (a) a microphone that picks up sound and converts the sound to an electrical signal, (b) an amplifier that amplifies the microphone electrical signal, and (c) a speaker that converts the amplified microphone electrical signal back to sound energy.

Internal feedback occurs when the sound energy generated by the speaker reaches the microphone at an intensity greater than that of the sound that was originally picked up by the microphone. The feedback path can be acoustic or mechanical or both acoustic and mechanical.

Acoustic feedback is most often the result of sound generated by speaker 26 passing through tube 32 and into housing 10 and finding a path through faceplate 13 back to microphone inlet 14. Because most hearing aid batteries require air to generate electricity, faceplate 13 is designed with openings that allow air to pass through and, as a consequence, sound also can pass through.

Mechanical feedback occurs because speaker 26 vibrates as it produces sound. These vibrations can travel through tube 32 to housing 10 or through resilient suspension 34 to housing 10 when the resilient suspension is in contact with the housing. In practice, it is difficult to maintain spaces 36 and 38 between resilient suspension 34 and housing 10. The designers of hearing aids strive to make hearing aids as small as possible so that the hearing aids can fit into the ear as far as possible. The mechanical vibrations conducted from resilient suspension 34 to housing 10 travel though the walls of the housing and ultimately cause a microphone 14 to vibrate. Movement of the diaphragm of microphone 14 relative to the wall of housing 10 causes microphone 14 to generate an electrical signal. Although designed to minimize the effect of such vibrations, microphone 14 cannot differentiate whether a movement is mechanical or acoustic.

Mechanical/acoustic feedback occurs when vibrations of speaker 26 cause vibration in housing 10. Some of these vibrations, in turn, generate sound energy that is picked up by microphone 14.

Selection of appropriate materials for tube 32 and resilient suspension 34 is important to prevent feedback. High durometer materials are good sound containers but transmit mechanical energy. Low durometer materials can isolate vibrations. However, low durometer materials are poor sound containers. If resilient suspension 34 makes contact with housing 10, mechanical energy can pass through. A thicker suspension helps but adds size. Allowing a greater space between resilient suspension 34 and housing 10 helps but also adds size. The designers of hearing aids constantly are faced with tradeoffs between physical size of the hearing aid and amplification by the hearing aid.

SUMMARY OF THE INVENTION

A hearing aid, constructed in accordance with the present invention, includes a housing having a sound inlet through which an outside sound enters the housing and a sound outlet through which an amplified version of the outside sound exits the housing. This hearing aid also has a battery within the housing and a microphone within the housing responsive to the outside sound entering the housing through the sound inlet for developing an electrical signal representative of the outside sound entering the housing. A hearing aid, constructed in accordance with the present invention, further includes an amplifier powered by the battery and responsive to the electrical signal for developing an amplified version of the electrical signal, an energy absorbing tip, and a speaker surrounded by the energy absorbing tip, responsive to the amplified version of the electrical signal for developing and conducting to the sound outlet the amplified version of the outside sound entering the housing, and rigidly mounted to the housing to channel acoustic energy and mechanical energy generated by the speaker to the energy absorbing tip.

According to another aspect of the present invention, the open end of the sound outlet from which sound emanates is remote from that end of the hearing aid that is innermost in the ear and closest to the ear canal of the person wearing the hearing aid.

BRIEF DESCRIPTION OF THE DRAWINGS

The present invention is best understood from the following detailed description when read in connection with the accompanying drawings.

DETAILED DESCRIPTION OF THE INVENTION

Figure 1:
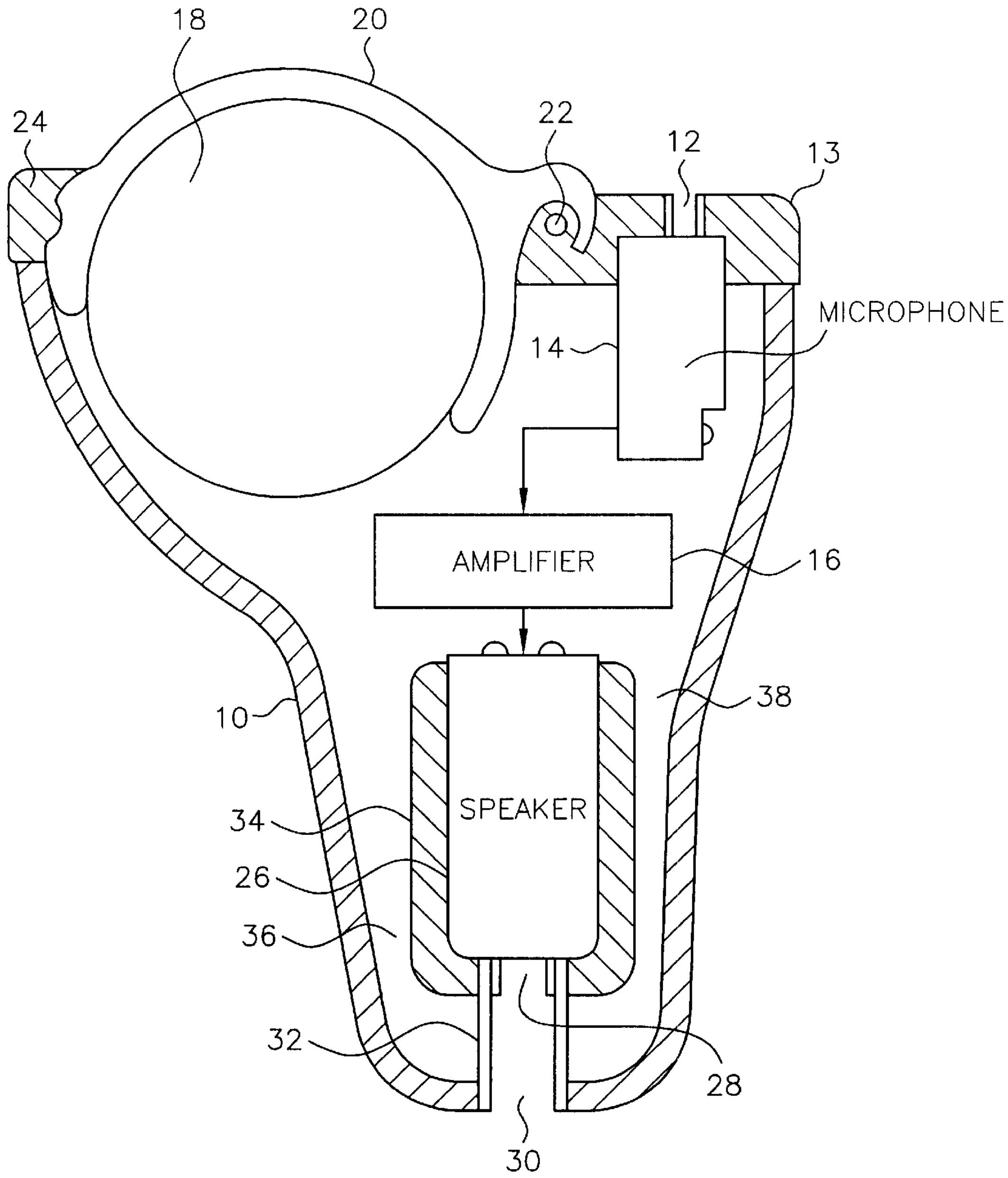
FIG. 1 is a cross-sectional view of a hearing aid of conventional construction and operation.
Figure 2:
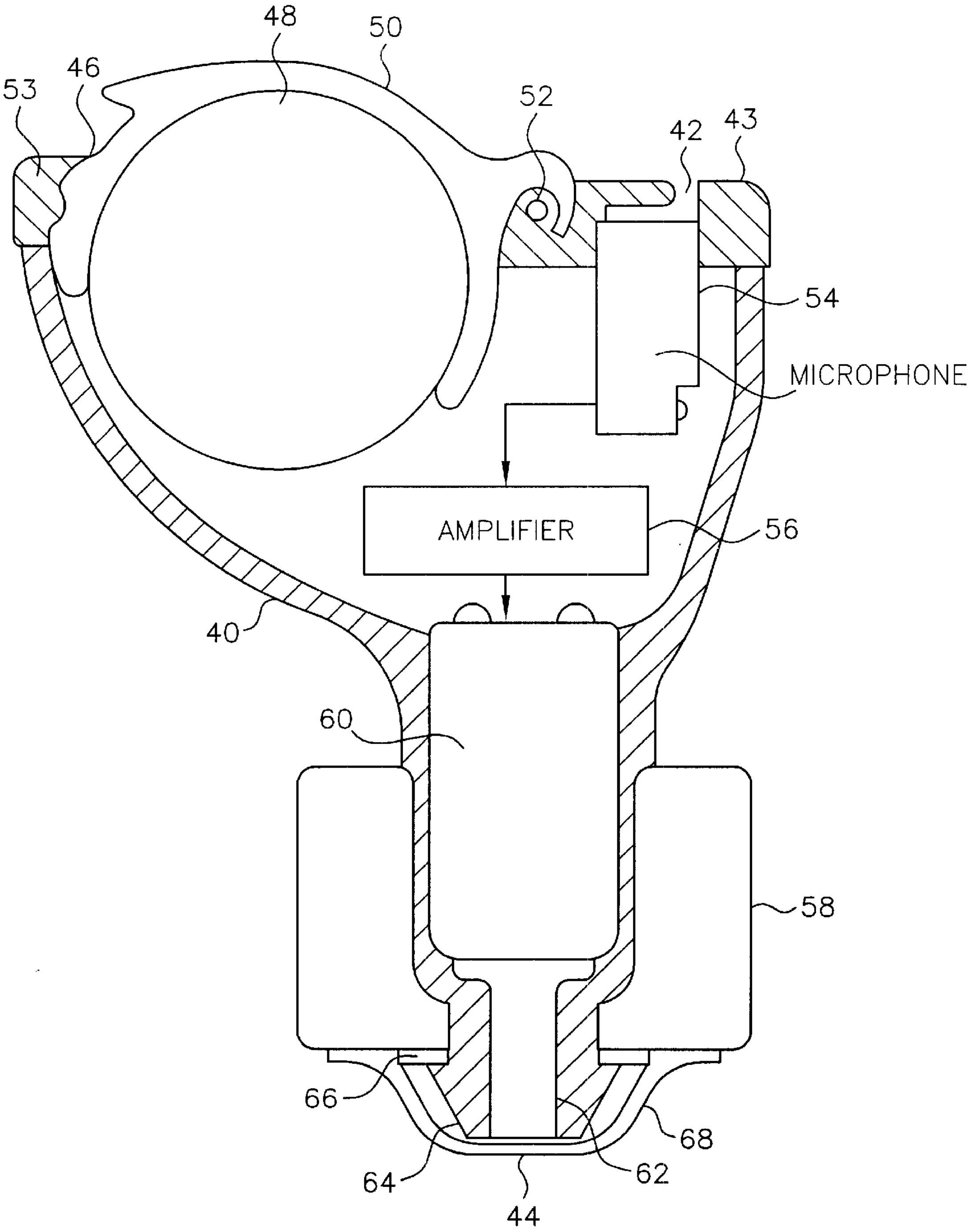
FIG. 2 is a cross-sectional view of a first embodiment of a hearing aid constructed in accordance with the present invention.

Referring to FIG. 2, a hearing aid, constructed in accordance with the present invention, includes a housing 40 having a sound inlet 42 extending through a faceplate 43 of the housing and through which outside sound enters the housing, a sound outlet 44 through which an amplified version of the outside sound exits the housing, and a battery inlet 46 through which a battery 48 is introduced into and removed from the housing. Because most hearing aid batteries require air to generate electricity, faceplate 43 is designed with openings that allow air to pass through.

A battery holder 50 is mounted to housing 40 in proximity to battery inlet 46 for pivotal movement about a hinge 52 between an open position that permits battery 48 to be introduced into and removed from the housing and a closed position that captivates the battery within the housing. Battery holder 50 is held in place by a battery snap 53 on housing 40.

It will be understood that a hearing aid, constructed in accordance with the present invention, can be arranged with a rechargeable battery that is sealed within the hearing aid housing and charged through terminals in a wall of the housing accessible from outside the housing. Such an arrangement does not require a battery holder, such as batter holder 15, nor a battery inlet, such as battery inlet 46.

A hearing aid, constructed in accordance with the present invention, also includes a microphone 54 within housing 40 responsive to the outside sound entering housing through sound inlet 42 for developing an electrical signal representative of the outside sound entering the housing. Also included in the FIG. 2 hearing aid is an amplifier 56 powered by battery 48 and responsive to the microphone electrical signal for developing an amplified version of the microphone electrical signal.

A hearing aid, constructed in accordance with the present invention, further includes an energy absorbing tip 58. This energy absorbing tip can be a foam material or other material that can absorb acoustic energy and mechanical energy generated by a speaker 60. For the FIG. 2 embodiment of the present invention, energy absorbing tip 58 surrounds housing 40, including tubular extension 62 of the housing. Energy absorbing tip 58 is fitted over housing 40 and held in place by a specially shaped end 64 of tubular extension 62 and a washer 66.

Speaker 60 is surrounded by energy absorbing tip 58. The extent over which energy absorbing tip 58 surrounds speaker 60 depends upon the design of the hearing aid and can be greater or less than illustrated in FIG. 2.

Speaker 60 is responsive to the amplified version of the electrical signal developed by amplifier 56 and develops and conducts to sound outlet 44 the amplified version of the outside sound entering housing 40.

Speaker 60 is rigidly mounted to housing 40 to channel acoustic energy and mechanical energy generated by the speaker to energy absorbing tip 58. The amplified version of the outside sound entering housing 40 is conducted from speaker 60 through tubular extension 62 of housing 40 into the ear canal of the person wearing the hearing aid.

As shown in FIG. 2, sound absorbing tip 58 includes a wax guard 68. Wax guard 68 extends across sound outlet 44 to inhibit wax from the ear of the person wearing the hearing aid to enter into and clog the sound outlet.

The hard mounting of speaker 60 to housing 40 and the presence of sound absorbing tip 58 surrounding the speaker inhibit mechanical energy and acoustic energy from returning to microphone 54. Generally, acoustic energy would return to the microphone by means of a path through air openings in faceplate 43. Generally, hard mounting speaker 58 to housing 40 would cause mechanical energy to travel through the walls of the housing and through faceplate 43 to microphone 54. Some of this mechanical energy would be converted to acoustic energy and find a pathway through faceplate 43 back to microphone 54 and cause feedback.

By reducing the thickness of the walls of housing 40 or even eliminating parts of the housing and incorporating energy absorbing tip 58 in the hearing aid to surround a portion of speaker 58, mechanical energy generated in the walls of housing 40 is absorbed by the energy absorbing tip. The walls of housing 40 can be made very thin because speaker 58 provides mechanical strength. With the specially shaped end 64 of tubular extension 62 of housing 40 attached to speaker 60 rather than being spaced from the speaker, a portion of the walls of housing 40 can be eliminated for a considerable portion of the speaker. Energy absorbing tip 58 also forms an acoustic seal in the ear of the person wearing the hearing aid.

As a result, a hearing aid, constructed in accordance with the present invention, having an energy absorbing tip and a speaker rigidly mounted to the housing of the hearing aid, when compared to conventional hearing aids, can be made considerably smaller, have higher amplification, and be simpler to assemble.

Figure 3:
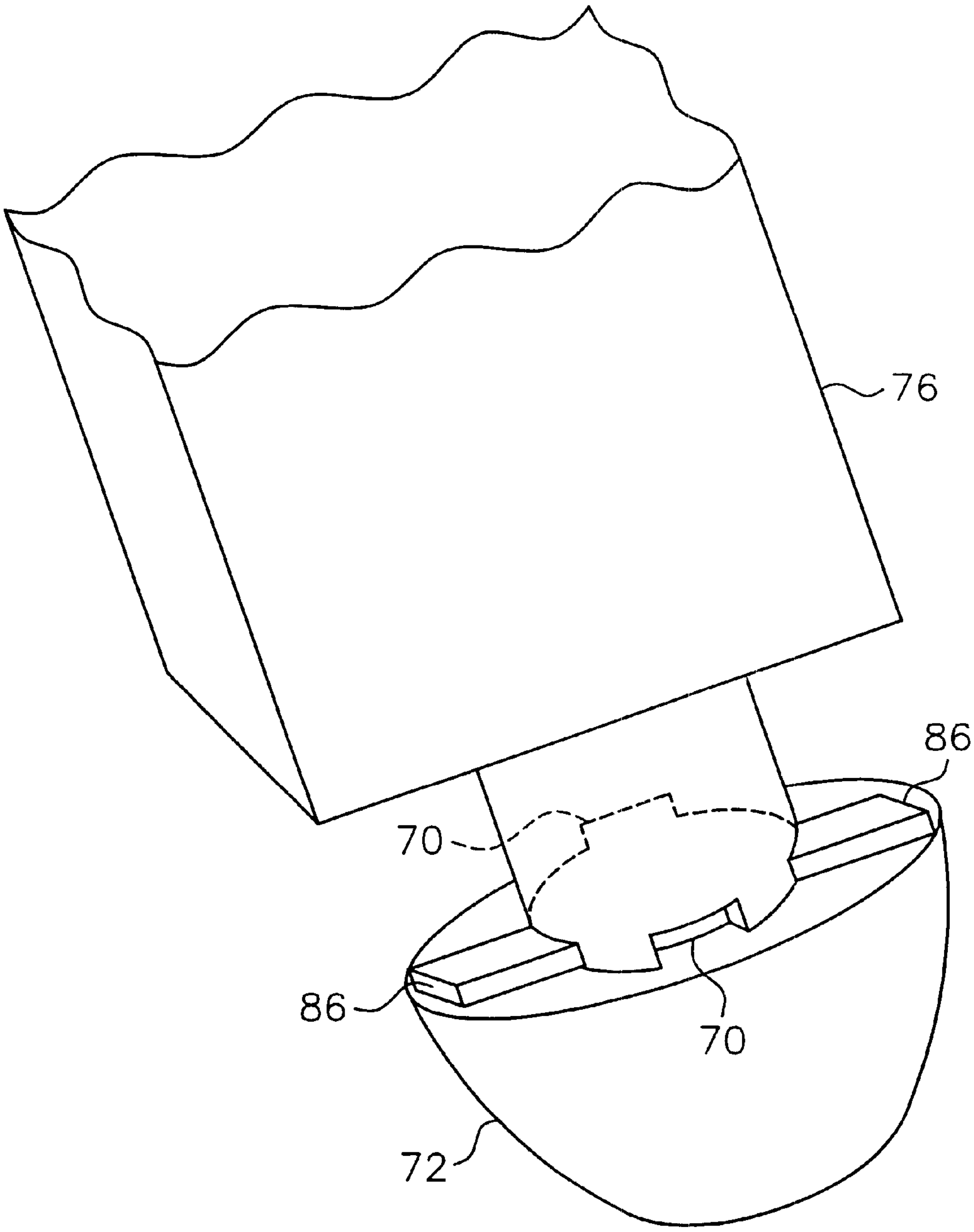
FIG. 3 is a perspective view of a portion of a second embodiment of a hearing aid constructed in accordance with the present invention.
Figure 4:
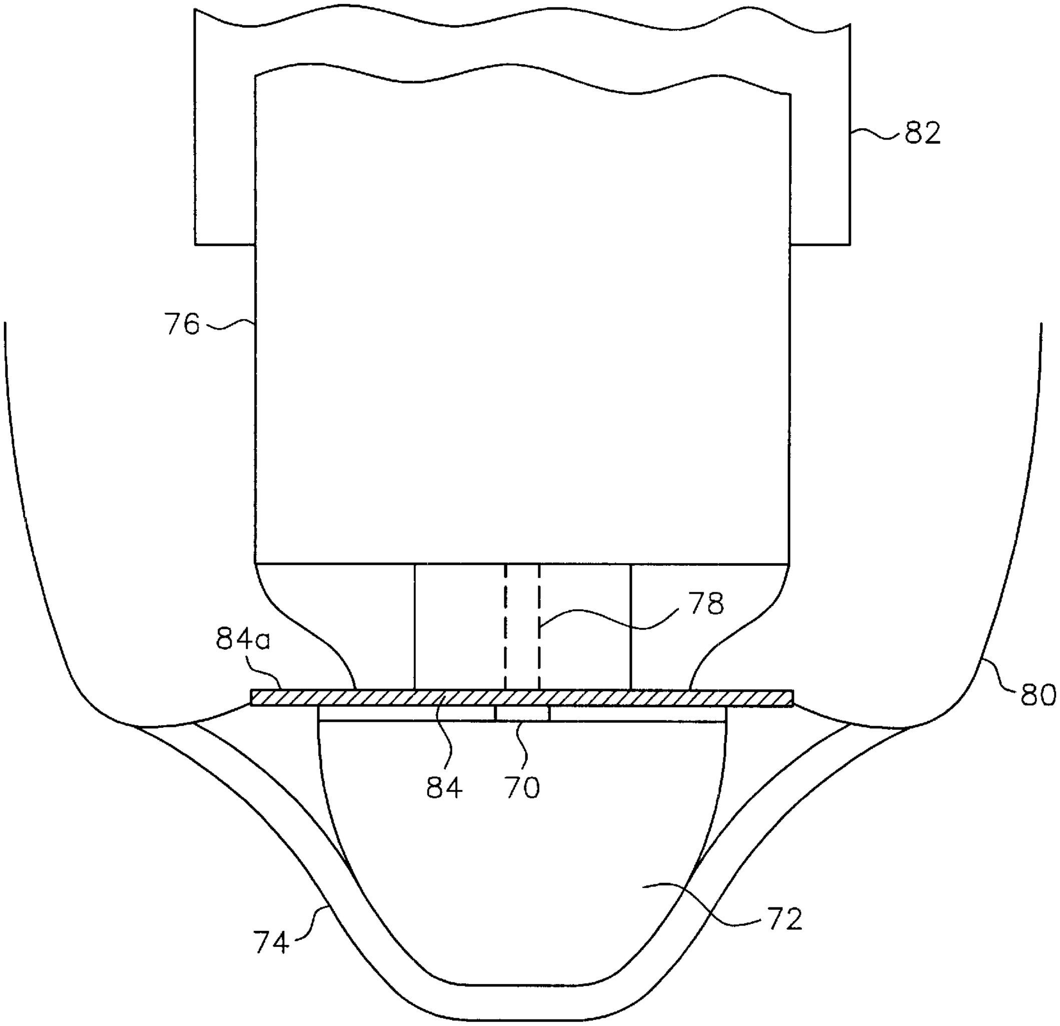
FIG. 4 is a cross-sectional view of the portion of the second embodiment of the present invention fitted with an energy absorbing tip.

FIGS. 3 and 4 show a portion of a second embodiment of a hearing aid constructed in accordance with the present invention. In this second embodiment of the present invention, the open end of the sound outlet, instead of being at that end of the hearing aid that is innermost in the ear and closest to the ear canal of the person wearing the hearing aid, is remote from that end of the hearing aid that is innermost in the ear and closest to the ear canal of the person wearing the hearing aid. Instead of the open end of the sound outlet being at the bottom end of a specially shaped end 64 of a tubular extension 62 of the hearing aid housing, as shown in FIG. 2, the open end of the sound outlet is at the top end of the specially shaped end in FIGS. 3 and 4. Despite the presence of a wax guard, such as wax guard 68 shown in FIG. 2, under certain circumstances, wax can penetrate the wax guard and enter the sound outlet of the speaker and clog the sound outlet.

In FIGS. 3 and 4, the open ends 70 of the sound outlet are located above a specially shaped end 72. The open ends 70 of the sound outlets are remote from that end of the hearing aid that is innermost in the ear and closest to the ear canal of the person wearing the hearing aid. Consequently, the probability of wax that penetrates a wax guard 74 entering and clogging the sound outlet is reduced. Sound exiting from a speaker 76 passes through a sound outlet that includes a tubular outlet passage 78 that extends away from speaker 76 and a pair of side outlet passages extending in opposite directions perpendicular to the tubular outlet passage and opening into open ends 70.

As with the FIG. 2 embodiment of the present invention, a sound absorbing tip 80 is provided as shown in FIG. 4. In FIG. 4, speaker 76 projects from a housing 82, so that sound absorbing tip 80 is fitted directly over speaker 76 with no housing wall between the speaker and the sound absorbing tip. As indicated above, by hard mounting speaker 76 to housing 82 in accordance with one important aspect of the present invention, a portion of the walls of the hearing aid housing can be eliminated for a considerable portion of the speaker.

Sound absorbing tip 80 is held in place by the shape of specially shaped end 72 and a washer 84. A first face 84a of washer 84 is attached to energy absorbing tip 80 between speaker 76 and the open ends 70 of the sound outlet. A pair of standoffs 86 are provided on the top of specially shaped end 72 upon which washer 84 rests, so that the open ends 70 of the sound outlet are not blocked. It should be noted that, while two open ends of the sound outlet are shown in FIG. 3, one or more than two open ends of the sound outlet can be provided.

Although illustrated and described herein with reference to certain exemplary embodiments, the preset invention, nevertheless, is not intended to be limited to the details shown and described. Rather, various modifications may be made to those exemplary embodiments within the scope and range of equivalents of the claims without departing from the invention.

What is claimed:

1. A hearing aid comprising:

a housing having:

(a) a sound inlet through which an outside sound enters said housing, and (b) a sound outlet through which an amplified version of the outside sound exits said housing to the ear canal of the person wearing the hearing aid;

a battery within said housing;

a microphone within said housing responsive to the outside sound entering said housing through said sound inlet for developing an electrical signal representative of the outside sound entering said housing;

an amplifier powered by said battery and responsive to the electrical signal for developing an amplified version of the electrical signal;

an energy absorbing tip; and a speaker:

(a) surrounded by said energy absorbing tip, (b) responsive to the amplified version of the electrical signal for developing and conducting to said sound outlet the amplified version of the outside sound entering said housing, and (c) rigidly mounted directly to said housing to channel acoustic energy and mechanical energy generated by said speaker to said energy absorbing tip.

2. A hearing aid according to claim 1 wherein said energy absorbing tip includes a wax guard.

3. A hearing aid according to claim 2 wherein said wax guard extends across said sound outlet.

4. A hearing aid according to claim 2 wherein:

(a) said sound outlet includes a tube extending away from said speaker, and (b) said energy absorbing tip surrounds said tube.

5. A hearing aid according to claim 1 wherein:

(a) said housing further has a battery inlet through which said battery is introduced into and removed from said housing, and (b) said hearing aid further includes a battery holder mounted to said housing in proximity to said battery inlet for pivotal movement between:

(1) an open position that permits said battery to be introduced into and removed from said housing, and (2) a closed position that captivates said battery within said housing.

6. A hearing aid according to claim 5 wherein:

(a) said sound outlet includes a tube extending away from said speaker, and (b) said energy absorbing tip surrounds said tube.

7. A hearing aid according to claim 6 wherein said energy absorbing tip includes a wax guard.

8. A hearing aid according to claim 7 wherein said wax guard extends across said sound outlet.

9. A hearing aid according to claim 4 further including a washer having a first face attached to said energy absorbing tip for holding said energy absorbing tip between said speaker and an open end of said sound outlet.

10. A hearing aid according to claim 3 wherein an open end of said sound outlet is at that end of said hearing aid that is innermost in the ear and closest to the ear canal of the person wearing the hearing aid.

11. A hearing aid according to claim 1 wherein said energy absorbing tip is a foam material.

12. A hearing aid according to claim 1 wherein said sound outlet includes:

(a) a tubular outlet passage extending away from said speaker and toward that end of said hearing aid that is innermost in the ear and closest to the ear canal of the person wearing the hearing aid and through which the amplified version of the outside sound passes from said speaker, and (b) a pair of side outlet passages extending in opposite directions perpendicular to said tubular outlet passage and through which the amplified version of the outside sound passes from said tubular outlet passage to exit said housing to the ear canal of the person wearing the hearing aid.

13. A hearing aid comprising:

a housing having a sound inlet through which an outside sound enters said housing;

a battery within said housing;

a microphone within said housing responsive to the outside sound entering said housing through said sound inlet for developing an electrical signal representative of the outside sound entering said housing;

an amplifier powered by said battery and responsive to the electrical signal for developing an amplified version of the electrical signal;

a speaker mounted to said housing and responsive to the amplified version of the electrical signal for developing an amplified version of the outside sound entering said housing;

a sound outlet to which the amplified version of the outside sound is conducted from said speaker for exiting from said hearing aid and having an open end remote from that end of said hearing aid that is innermost in the ear and closest to the ear canal of the person wearing said hearing aid; and an end member between said open end of said sound outlet and that end of said hearing aid that is innermost in the ear and closest to the ear canal of the person wearing said hearing aid; and a wax guard extending over said end member and toward said speaker to inhibit wax from entering space between said open end of said sound outlet and that end of said hearing aid that is innermost in the ear and closest to the ear canal of the person wearing said hearing aid.

14. A hearing aid according to claim 13 wherein said sound outlet includes a tubular outlet passage extending away from said speaker and a pair of side outlet passages extending in opposite directions perpendicular to said tubular outlet passage.

15. A hearing aid according to claim 14 further including an energy absorbing tip of foam material surrounding at least a portion of said speaker and said sound outlet.

16. A hearing aid according to claim 15 further including a washer having a first face attached to said energy absorbing tip for holding said energy absorbing tip between said speaker and said open end of said sound outlet.

17. A hearing aid according to claim 13 wherein:

(a) said housing further has a battery inlet through which said battery is introduced into and removed from said housing, and (b) said hearing aid further includes a battery holder mounted to said housing in proximity to said battery inlet for pivotal movement between:

(1) an open position that permits said battery to be introduced into and removed from said housing, and (2) a closed position that captivates said battery within said housing.

18. A hearing aid according to claim 13 further including an energy absorbing tip of foam material surrounding at least a portion of said speaker and said sound outlet.

19. A hearing aid according to claim 18 wherein said speaker projects from said housing and said energy absorbing tip is fitted directly over said speaker and surrounds said speaker.

20. A hearing aid according to claim 19 further including a washer having a first face attached to said energy absorbing tip for holding said energy absorbing tip between said speaker and said sound outlet.

21. A hearing aid according to claim 20 wherein said sound outlet includes a tubular outlet passage extending away from said speaker and a pair of side outlet passages extending in opposite directions perpendicular to said tubular outlet passage.

22. A hearing aid comprising:

a housing having a sound inlet through which an outside sound enters said housing;

a microphone within said housing responsive to the outside sound entering said housing through said sound inlet for developing an electrical signal representative of the outside sound entering said housing;

a battery within said housing;

an amplifier powered by said battery and responsive to the electrical signal for developing an amplified version of the electrical signal;

a speaker responsive to the amplified version of the electrical signal for developing an amplified version of the outside sound entering said housing; and a sound outlet having:

(a) a tubular outlet passage extending away from said speaker and toward that end of said hearing aid that is innermost in the ear and closest to the ear canal of the person wearing the hearing aid and through which the amplified version of the outside sound passes from said speaker, and (b) a pair of side outlet passages extending in opposite directions perpendicular to said tubular outlet passage and through which the amplified version of the outside sound passes from said tubular outlet passage to exit said housing to the ear canal of the person wearing the hearing aid.

* * * * *